United States Patent [19]

Elsenbaumer et al.

[11] 4,392,978
[45] Jul. 12, 1983

[54] SELECTIVE AROMATIC NITRATION

[75] Inventors: Ronald L. Elsenbaumer, Morristown; Edel Wasserman, Summit, both of N.J.

[73] Assignee: Allied Corporation, Morris Township, Morris County, N.J.

[21] Appl. No.: 107,235

[22] Filed: Dec. 26, 1979

[51] Int. Cl.$^3$ .................. C09K 3/00; C07B 11/00; C07D 323/00
[52] U.S. Cl. .................. 252/182; 549/351; 549/352; 549/353; 568/939; 568/940; 260/688
[58] Field of Search .................. 260/338, 340.3, 688; 252/182; 568/940, 939

[56] References Cited

U.S. PATENT DOCUMENTS

| | | | |
|---|---|---|---|
| 3,562,295 | 2/1971 | Pedersen | 260/338 |
| 3,594,985 | 7/1971 | Ameen et al. | 55/44 |
| 3,686,225 | 8/1972 | Pedersen | 260/340.3 |
| 3,687,978 | 8/1972 | Pedersen | 260/340.3 |
| 3,997,562 | 12/1976 | Liotta | 260/338 |
| 3,997,563 | 12/1976 | Dale et al. | 260/338 |

OTHER PUBLICATIONS

James W. Zubrick et al., Tetrahedron Letters No. 1 (1975), pp. 71–74.
C. J. Pedersen, Jour. Am. Chem. Soc., Dec. 20, 1967, vol. 89:26, pp. 7017–7036.
Kirk–Othmer; "Encyclopedia of Chemical Technology", A. Standen, Ed., vol. 13, pp. 784–796, and 844–846, 2nd Ed., InterScience Publishers, New York.
"Industrial and Laboratory Nitrations", L. F. Albright and C. Hanson, Eds., ACS Symposium Series, vol. 22, pp. 2–7, American Chem. Society, Wash., D.C. (1976).
C. L. Coon et al., J. Org. Chem., vol. 25, pp. 4243–4248 (1973).
R. Breslow, "Organic Reaction Mechanisms", W. A. Benjamin, Inc., 2nd Ed., New York, NY, 1969, p. 148.
G. A. Olah, "Fundamental Study of Toluene Nitration", U.S. NTIS; AD–AO21–145 (1975).
E. V. Dehmlow, Angew. Chem. Int. Ed., Engl., vol. 16, (8) 493–505 (1977) at p. 494.
L. L. Chan et al., J. American Chem. Society, vol. 92(7) pp. 1955–1963 (1970).
C. J. Pedersen et al., Angew. Chem. Int. Ed. Engl., vol. 11(1), pp. 16–25 (1972).
U. Takaki et al., J. Amer. Chem. Soc., vol. 96(8), pp. 2588–2593 (1974).
C. J. Pedersen, J. American Chem. Soc., vol. 92(2), pp. 391–394, (1970).

*Primary Examiner*—Norma S. Milestone
*Attorney, Agent, or Firm*—Thomas D. Hoffman; Robert A. Harman

[57] ABSTRACT

A method and reagent for the selective nitration of aromatic hydrocarbons which comprises contacting a complex of at least a catalytic amount of a polyether with a nitronium containing substance, e.g., NO$_2$BF$_4$ with an aromatic hydrocarbon, e.g., toluene with at least one replaceable hydrogen. Nitration of toluene with these complexes at ambient temperature resulted in a reduction in meta substitution. In competitive studies, soluble crown ether complexes of NO$_2$BF$_4$ in CH$_2$Cl$_2$ nitrated toluene 45–59 times faster than they nitrated benzene.

10 Claims, No Drawings

SELECTIVE AROMATIC NITRATION

BACKGROUND

1. Field of Search

This invention relates to a selective reagent and method for aromatic nitration. More particularly this invention relates to a method of aromatic nitration by use of a reagent which is a complex of a nitronium containing substance and a polyether, which method exhibits high positional and substrate selectivity.

2. Prior Art

The nitration of aromatic hydrocarbons is an important industrial process. Of particular importance is the nitration of toluene for the production of toluene diisocyanates.

A common aromatic nitration is the reaction of toluene with $HNO_3/H_2SO_4/H_2O$ to produce a mixture of isomeric nitrotoluenes having the following composition: 33–34% p-nitrotoluene, 3–4% m-nitrotoluene and 62–63% o-nitrotoluene. Separation of the mixture into its components entails complicated physical methods. See, Kirk-Othmer, Encyclopedia of Chemical Technology, Anthony Stander, Ed., Vol. 13, p. 845, 2nd Edition, Interscience Publishers, New York, N.Y.

A large body of literature is directed to efforts to alter the positional and substrate selectivity in aromatic nitration ("Industrial and Laboratory Nitrations", L. F. Albright and C. Hanson, Eds., ACS Symposium Series, Vol. 22, American Chemical Society, Washington, D.C., 1976).

Aromatic hydrocarbons, e.g., benzene, toluene are commonly nitrated by mixtures of nitric and sulfuric acid. A variety of evidence indicates that the nitronium ion, $NO_2^+$, is formed and is the actual nitrating agent. (Ronald Breslow, Organic Reaction Mechanisms, W. A. Benjamin, Inc., 2nd Ed. of New York, N.Y. 1969, p. 148).

A variety of nitronium containing nitrating agents e.g., $NO_2BF_4$, $NO_2PF_6$ and $NO_2[CF_3SO_3]$ have been used to alter the radio of ortho to para substitution and the amount of meta product. (C. L. Coon, W. G. Blucher and M. E. Hill, J. Org. Chem., Vol. 38, No. 25, p. 4243–4448 (1973); G. A. Olah, "Fundamental Study of Toluene Nitration", U.S. NTIS, AD-AO21-145, 1976). However, reduction in the amount of meta substitution to a value below 2% of the total mixture of mononitration products was usually effected by lowering the reaction temperature. It would be desirable to mimick this temperature effect by chemical means.

A comprehensive survey of a large number of methods of mononitration of toluene has been made by Olah (Fundamental Study of Toluene Nitration NTIS, AD-AO21-145). While some of the reagents surveyed were complexes of various nitronium containing substances, e.g., $NO_2PF_6$, $NO_2BF_4$, etc., with alcohols, dialkyl ethers, dialkyl sulfide, tetrahydrofuran and substituted pyridines, the percentage of meta nitrotoluene in the product mixture generally exceeded 3%. None of the reagents surveyed combined positional and substrate selectivity.

Macrocyclic polyethers, e.g., crown ethers are known to complex metal cations, especially alkali, alkaline earth and various transition metal cations and thereby enhance the reactivity of the counter anions. U.S. Pat. Nos. 3,562,295 (C. J. Pedersen) and 3,997,563 (J. Dale et al.). The use of crown ethers as phase-transfer catalysts is disclosed by E. V. Dehmlow in Angew. Chem. Int. Ed. Engl., Vol. 16, No. 8, at page 494 (1977).

The complexation of lithium, sodium and potassium ions by dimethyl ethers of polyethylene glycols is disclosed by L. L. Chan et al. in The Journal of The American Chemical Soc., Volume 92, No. 7 at page 1955 (1970). None of these references discloses an aromatic nitrating agent which is substrate selective and effectively reduces the amount of meta substitution.

It is accordingly an object of the present invention to provide a process for the selective nitration of aromatic hydrocarbons at ambient temperatures.

It is another object of the present invention to provide a process for the mononitration of aromatic hydrocarbons with minimal meta substitution.

It is still further an object of the present invention to provide an aromatic nitrating agent which is positional and substrate selective.

SUMMARY OF THE INVENTION

In accordance with the present invention, there is provided a reagent and method for the selective aromatic nitration which comprises complexing a substance containing a nitronium ion with at least a catalytic amount of a polyether, contacting the complex so formed with an aromatic hydrocarbon having at least one replaceable hydrogen. In general, these aromatic nitrations are performed in a solvent by the addition of the aromatic hydrocarbon to a preformed polyether—$NO_2^+$ complex at a temperature from about $-20°$ to about $40°$ C. Reduction in the amount of meta substitution to less than about 0.6 to about 1.6% of the total mixture of mononitroaromatic products has been achieved when even as little as a catalytic amount of polyether, e.g., polyethylene oxide having an average molecular weight of about 100,000 is used, to complex the nitronium containing substance. The polyether is not destroyed but can be recovered and recycled.

DETAILED DESCRIPTION OF THE INVENTION

In accordance with the present invention there is provided a reagent and method for the selective nitration of aromatic hydrocarbons wherein a preformed complex of a nitronium containing substance and at least a catalytic amount of a polyether is contacted with an aromatic hydrocarbon. The reagents prepared in accordance with the present invention show high positional selectivity; they are effective in reducing the amount of meta substitution (0.6 to 2.3%, preferably 0.6–1.6% by weight meta nitrotoluene) in nitrations of toluene compared to nitrations performed without added polyether. In competitive reactions, the reagent complexes of the present invention also exhibit high substrate selectivity; these preformed complexes nitrated benzene 45 to 59 times slower than they nitrated toluene.

The nitronium containing substance is selected from the group consisting of nitronium salts, alkanoyl nitrates, $HNO_3/H_2SO_4/H_2O$, $HNO_3/H_2O$, and $CF_3SO_3H/HNO_3$. The nitronium salts have the formula $NO_2Y$ wherein Y is $AlCl_4^-$, $BF_4^-$, $PF_6^-$, $AsF_6^-$, $SbCl_6^-$, $SnCl_5^-$, $TiCl_5^-$, $CF_3SO_3^-$, $HS_2O_7^-$, $HSO_4^-$ or $KSO_4^-$. Useful nitronium salts are preprepared by contacting $NO_2X$ with $AgBX_4$, $BX_3$, $AsX_5$, $AlX_3$, $PX_5$, $SbX_5$, $SnX_4$ or $TiX_4$ wherein X is F, Cl, Br, I or $(NO_2)_3C$, preferably F. A preferred nitronium salt is $NO_2BF_4$ which can be prepared in high purity by contacting HNO₃/HF with BF₃ as described by G. A. Olah et al. in Org. Syn., Coll. Vol. 5 at p. 480. The alkanoyl nitrates have the formula RCOONO₂ wherein R represents alkyl, aryloxy methylene, alkyloxy methylene, or trifluoromethyl, wherein alkyl has one to five carbons and aryl is pentafluorophenyl or nitrophenyl. A preferred alkanoyl nitrate is acetyl nitrate.

The polyether is selected from the group consisting of macrocyclic polyethers, polyalkylene oxides and dialkyl ethers of polyalkylene glycols. The macrocyclic polyethers can be dicyclohexano-18-crown-6 and crown ethers having from 4 to 10 -O-M- units wherein M for a particular macrocyclic polyether is

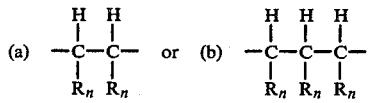

wherein each $R_n$ is independently selected from the group consisting of hydrogen or an alkyl group consisting of 1 to 4 carbons or wherein one M is (b) and the remaining are (a). The R groups are preferably H. The dicyclohexano crown ethers can be either the cis-syn-cis-isomer (the meso isomer) or the cis-anti-cis isomer (the d, l isomer). Generally, the crown ethers useful in the invention contain from 12 to 30 atoms in the polyether ring. The preferred crown ethers are those containing 12 to 18 atoms in the polyether ring. Typical examples of preferred crown ethers are at least one of the members selected from the group 12-crown-4, 15-crown-5, 18-crown-6 and, meso and d, l-dicyclohexano-18-crown-6. The system of nomenclature used for crown ethers is explained in Pederson, J. Am. Chem. Soc., 89, 7017 (1967). A general procedure for the preparation of crown ethers, disclosed in U.S. Pat. No. 3,562,295 issued on Feb. 9, 1971 to Pedersen is hereby incorporated by reference.

The polyalkylene oxides useful in the present invention are selected from the group wherein the alkylene group consists of 2 or 3 carbons. The preferred polyalkylene oxides are polyethylene oxides having an average molecular weight of at least about 100,000.

The dialkyl ethers of polyalkylene glycols found useful in the present invention have alkyl groups having from 1 to 8 carbons, alkylene groups having 2 or 3 carbons and have from 2 to about 5,000 alkylene groups. The preferred dialkyl ethers have 1 to 8 carbon atoms in each alkyl group and 2 to 8 ethylene units. Typical examples of suitable dialkyl ethers include, diglyme (CH₃O(C₂H₄O)₂CH₃), triglyme (CH₃O(C₂H₄O)₃CH₃), tetra glyme (CH₃O(C₂H₄O)₄CH₃), and the mixtures of dimethyl ethers of polyethylene glycols of the formula CH₃O(C₂H₄O)$_t$CH₃ wherein t is between 2 and 9, preferably between 3 and 9. The preferred homolog distribution of CH₃(OC₂H₄O)$_t$CH₃ is approximately as follows:

| t | Weight % of Homolog in Mixture |
|---|---|
| 3 | 4–9 |
| 4 | 22–24 |
| 5 | 24–28 |
| 6 | 20–22 |
| 7 | 13–15 |
| 8 | 6–8 |
| 9 | 2–4 |

The preparation of the mixtures of homologs, disclosed in U.S. Pat. No. 3,594,985 which was issued on July 27, 1971 to J. Ameer et al. at Col. 2, lines 66 to Col. 3, line 10 and at Col. 5, lines 71–72 is hereby incorporated by reference.

The aromatic hydrocarbon compounds found useful with the reagent and method of the present invention have at least one replacable hydrogen and are represented by the formula

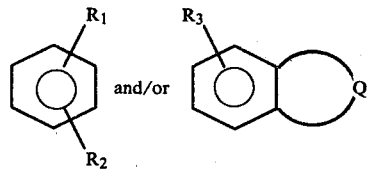

wherein $R_1$, $R_2$, and $R_3$ are independently selected from the group consisting of H, phenyl, benzyl, tolyl, naphthyl and alkyl groups having from 1 to 8 carbons, and wherein Q represents

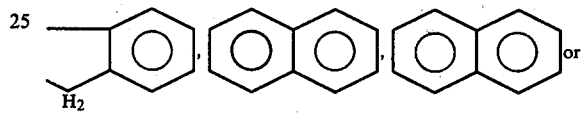

Typical aromatic hydrocarbon compounds include benzene, toluene, isomeric xylenes, ethylbenzene, cumene, biphenyl, napthalene, anthracene, penanthrane, fluorene.

A particularly important compound is toluene.

The solvents well known in the field of electrophilic aromatic substitution, e.g. nitrations and Friedel-Craft substitution reactions have been found useful in the method and reagent of the present invention. Typical solvents include polyhaloalkanes having 1 to 8 carbons, halogenated hydrocarbons e.g, CH₂Cl₂, CHCl₃, SO₂, CH₃NO₂, CH₃CN, CS₂, tetramethylene sulfone having the formula (CH₂)₄ SO₂, the above described aromatic hydrocarbons, H₂SO₄, HNO₃, H₂O and mixtures thereof. Of course solvents, e.g., sulfides, which interfere with the process of the present invention are to be avoided.

It is one of the features of the present invention that complete homogeneity is not essential for the method of the present invention. It has been discovered that only a catalytic amount of the polyether is required to dissolve solid nitronium containing substances or complex the nitronium ion in the liquid phase. Many of the reactions listed in Tables I–III (below) are examples of phase transfer catalysis between solids and liquid phases. It is another feature of the present reaction that the polyether is not destroyed under the conditions of the present invention.

In a preferred embodiment of the present invention, the nitronium containing substance is NO₂BF₄ and the polyether is a crown ether as described above. These preformed crown ether nitronium complexes appeared stable under conditions of the present invention. Specifically, the 18-crown-6 and 15-crown-5 nitronium complexes in substantially moisture-free $CH_2Cl_2$ showed no signs of decomposition after storage for 3 weeks under a nitrogen atmosphere at 25° C. However, the 12-crown-4 complex gave a tar under similar conditions. In one experiment (Example 3 in Table I) 18-crown-6 was recovered in crystalline form in 85% yield. All of the crown ethers showed some decomposition after prolonged contact with $HBF_4$ liberated from $NO_2BF_4$.

In accordance with the present invention, the molar ratio of the aromatic compound to the preformed nitronium containing substance is conveniently varied from 1:1 to 100:1 preferably from 1:1 to 10:1.

The reaction temperature for the aromatic nitrations in accordance with the present invention may be from about $-20°$ to about 40° C., preferably from about 0° to about 40° C., more preferably about 20° to about 25° C. When $SO_2$ is employed as the solvent at 20°-40° C. it is convenient to operate under an applied pressure of about 310–552 Pa (45–80 psi).

The reagent for selective aromatic nitration in accordance with the present invention consists of a preformed complex of a nitronium containing substance and at least a catalytic amount of a polyether as described above. In accordance with the invention the preformed polyether—$NO_2^+$ complexes are prepared by mixing a nitronium containing substance with at least a catalytic amount of a polyether, preferably by adding the polyether to the nitronium containing substance, more preferably adding the polyether in substantially moisture-free solvent to a nitronium containing substance. Typically the nitronium containing substance is one of the members selected from the group consisting of $NO_2BF_4$, $NO_2PF_6$, $NO_2SbF_6$, $NO_2SF_6$, $NO_2CF_3SO_3$, $NO_2SnF_6$ and $NO_2AsF_6$. While $NO_2BF_4$ is the preferred nitronium containing substance it is to be understood that other nitronium containing substances, described above, are considered within the scope of the present invention. Any convenient solvent described hereinabove can be employed, preferably substantially moisture-free $CH_2Cl_2$. Since the nitronium containing substances are typically hydroscopic, substantially moisture-free solvents are preferred. In accordance with the process of the present invention a solution of the above-described aromatic hydrocarbon in at least one of solvents described above, preferably $CH_2Cl_2$, is added to the preformed complex at any convenient temperature from about $-20°$ to about 40°, preferably about 0° to about 40° C., more preferably about 20°-25° C.

While only at least about a catalytic amount of the polyether is needed for operation of the reagent in the process of the present invention, it has been found convenient to employ at least about 0.1 mole of crown ether, e.g., 18-crown-6 per mole of nitronium containing substance and at least about $2 \times 10^{-3}$ moles of the polyalkyleneoxide having an average molecular weight of at least about 100,000 per every mole of the nitronium compound.

The stoichiometry in the soluble complexes of crown ethers and $NO_2BF_4$ in $CH_2Cl_2$ has been determined to be about 0.92 moles of 18-crown-6 per mole of $NO_2^+$ and about 3.0 moles of 12-crown-4 per mole of $NO_2^+$. While the stoichiometry of the 15-crown-5 complex of $NO_2BF_4$ in $CH_2Cl_2$ is not well defined, a minimum of about 1.7 moles of 15-crown-5 was required to completely solubilize every mole of $NO_2BF_4$ in $CH_2Cl_2$.

To test the substrate selectivity of the soluble crown ether complexes of $NO_2BF_4$, to a tenfold excess of a 1:1 molar ratio of benzene and toluene was added the aforementioned soluble crown ether complexes. The results listed in Table II indicate that crown ether complexes of $NO_2BF_4$ prepared in accordance with the present invention, nitrated toluene 45–59 times faster than they nitrated benzene. Thus, these complexes showed substantially increased substrate selectivity over noncomplexed $NO_2BF_4$ disclosed by G. A. Olah and N. A. Overchuck in Can. J. Chem, Volume 43, page 3279 (1965).

EXPERIMENTAL METHODS

Reagents: Crown ethers were obtained from Aldrich Chemical Co. or can be synthesized by the methods described in U.S. Pat. No. 3,562,295 (Pederson) at Col. 5 lines 27 to Col. 8, line 7, and U.S. Pat. No. 3,687,978 (Pedersen) which are hereby incorporated by reference. The preparation of these crown ethers are also described in two articles by C. J. Pedersen in the J. of the American Chemical Society: Vol. 89 pages 7017–7036 (1967) and Vol. 92 pages 391–394 (1973) which are hereby incorporated by reference.

The preparation of $NO_2BF_4$ is described in Fieser and Fieser, Reagents for Organic Synthesis J. P. Wiley, New York, N.Y. 19 Vol. I, p. 742. $NO_2BF_4$ obtained commercially contained from 17% to 50% $NOBF_4$ as an impurity. Under the experimental conditions of the method of this invention, $NOBF_4$ did not react with toluene. The yields of mononitrotoluenes with uncomplexed $NO_2BF_4$ were generally 65–80%.

The infrared spectra were recorded as $CH_2Cl_2$ solutions using AgCl windows in 0.01 mm thick cells.

The gas-liquid chromatographic (glc) analysis were performed on a Hewlett-Packard gas chromatograph model 5711A equipped with a 1.83 m×2 mm glass column, 8% Carbowax 20 M on Chromasorb W80–100 mesh; column, 170° C.; injector, 200° C.; detector, 350° C.; $N_2$ flow rate, 30 ml/min; flame ionization detector; retention times were: nitrobenzene, 7.6 min; ortho-nitrotoluene, 8.7 min; meta-nitrotoluene, 10.6 min; paranitrotoluene 12.2 min. Dinitrotoluenes and crown ethers were analyzed by temperature programming, 155° to 230° @16°/min. Yields were determined by internal standard (n-pentadecane).

Conductometric titrations were performed with a dip-type conductivity cell with platinum electrodes (Yellow Springs Instrument Co., Model No. 3403) using a method described in D. A. Skoog and D. M. West, "Fundamentals of Analytical Chemistry 2nd ed,. Hott, Rinehart and Winston, Inc. New York, N.Y., 1969, p. 570.

GENERAL EXPERIMENTAL METHOD FOR EXAMPLES 1–21

Nitrations without Complexing Agent: These experiments were performed by adding toluene (3.4 mmol, 312 mg) in the indicated solvent to $NO_2BF_4$ (226 mg, 1.71 mmol) in 3 ml of the dry solvent at the specified temperature. The reaction mixture was stirred for 30 min. at constant temperature. After treatment with water (2 ml), the layers were separated, and the dried organic layer analyzed by gas-liquid chromatography. The experiments in $CH_3CN$ and $SO_2$ were homogeneous; when $CH_2Cl_2$ was the solvent, the reaction was heterogeneous. Nitrations with Crown Ethers: These experiments were performed at the specified temperature in the indicated solvent by addition of toluene (312 mg, 3.4 mmol) in 0.5 ml of the specified dry solvent to a preformed crown ether—$NO_2^+$ complex prepared by adding 0.17 to 5.13 mmol of crown ether in 1.5 ml of dry solvent to $NO_2BF_4$ (226 mg, 1.71 mmol) in 2 ml of solvent. With 18-crown-6 in $CH_2Cl_2$, the formation of the soluble nitronium ion complex was quite rapid (1–2 min at 20° C.) even though $NO_2BF_4$ is completely insoluble in this solvent. Complex formation with 12-crown-4 was slower, requiring 10 min for complete solubilization. Complex formation with 15-crown-5 was exceptionally slow requiring hours for complete solubilization. All these complexes rapidly nitrated toluene at room temperature with the formation of $HBF_4$. The crown ethers generally underwent little decomposition; in one experiment (Run 3 in Table I), 18-crown-6 was recovered in crystalline form in 85% yield. The reactions were quenched with water and the dried organic layers analyzed by glc. The % conversion of mononitrotoluenes ranged from 50–70%.

NITRATION IN THE PRESENCE OF $NO_2 BF_4$ AND POLYETHYLENE OXIDE

A solution of 0.180 g of polyethylene oxide having an average molecular weight of about 100,000 and 0.10 g (0.755 mmol) of $NO_2BF_4$ in 3 ml of $CH_2Cl_2$ was used to nitrate 92 mg (1 mmol) of toluene at 20° C. After 30 min. the reaction mixture was quenched with water. Results of glc analysis are displayed in Table I.

NITRATION IN THE PRESENCE OF $NO_2BF_4$ AND DIGLYME

EXAMPLE 20

To a suspension of 166.1 mg (1.25 mmole) of $NO_2BF_4$ in 3 ml of $CH_2Cl$ was added 180 ml (167.8 mg, 1.25 mmole) of diglyme. The resulting pale yellow solution with suspended white powder was stirred for 30 min. at room temperaature (20°–21° C.). A solution of toluene (115.3 mg, 1.25 mmole) in 1.5 ml $CH_2Cl_2$ was slowly added. After 2 hr. at room temperature, the mixture was worked up by the addition of sat'd $K_2CO_3$. The organic layer was analyzed by glc using n-pentadecane as an internal standard. The results are shown in Table I.

EXAMPLE 21

The above procedure was repeated using 262. mg (1.98 mmole) of $NO_2BF_4$ and 1.59 g (11.8 mmole) of diglyme. This amount of diglyme was needed to completely solubilize all of the $NO_2BF_4$. To the soluble complex in $CH_2Cl_2$ was added 273 mg (2.97 mmole) of toluene as a solution in 0.5 ml of $CH_2Cl_2$. After 15 min. the reaction was worked up by the addition of water and analyzed as above. The results are listed in Table 1.

TABLE I

Toluene Nitration with $NO_2BF_4$ in the Presence of Polyethers

| Run | Solvent | Temp. | Poly Ether | Poly Ether(a) / $NO_2^+$ | % meta(b) (+0.2) | o/p(c) |
|---|---|---|---|---|---|---|
| 1 | $CH_2Cl_2$ | 23° C. | none | (d) | 2.5 | 1.55 |
| 2 | $CH_2Cl_2$ | 23° C. | 18-crown-6 | 0.1(d) | 1.4 | 1.50 |
| 3 | $CH_2Cl_2$ | 21° C. | " | 1.0(e) | 0.8 | 1.65 |
| 4 | $CH_2Cl_2$ | 0° C. | " | 1.0(e) | 1.0 | 1.74 |
| 5 | $CCl_4$ | 22° C. | " | 1.0(d) | 1.7 | 1.09 |
| 6 | $SO_2$ | −10° C. | none | —(e) | 2.5 | 1.84 |
| 7 | $SO_2$ | −10° C. | 18-crown-6 | 1.0(e) | 1.3 | 2.10 |
| 8 | $SO_2$ | −10° C. | " | 2.0(e) | 1.1 | 1.75 |
| 9 | $CH_3CN$ | 22° C. | none | —(e) | 2.3 | 2.27 |
| 10 | $CH_3CN$ | 22° C. | 18-crown-6 | 1.0(e) | 1.6 | 2.44 |
| 11 | $CH_2Cl_2$ | 23° C. | 15-crown-5 | 0.1(d) | 1.6 | 1.33 |
| 12 | $CH_2Cl_2$ | 20° C. | " | 1.7(e) | 1.4 | 1.45 |
| 13 | $CH_2Cl_2$ | 23° C. | 12-crown-4 | 0.1(d) | 2.3 | 1.40 |
| 14 | $CH_2Cl_2$ | 23° C. | " | 1.0(d) | 0.6 | 1.51 |
| 15 | $CH_2Cl_2$ | 20° C. | " | 3.0 | 0.8 | 1.57 |
| 16 | $CCl_4$ | 24° C. | " | 1.0(d) | 2.7 | 1.36 |
| 17 | $CH_2Cl_2$ | 23° C. | dicyclo-hexyl-18-crown-6(A)(f) | 1.0(e) | 1.4 | 1.59 |
| 18 | $CH_2Cl_2$ | 23° C. | dicyclo-hexyl-18-crown-6(B)(g) | 1.0(e) | 0.9 | 1.67 |
| 19 | $CH_2Cl_2$ | 20° C. | polyethylene oxide | —(h) | 0.8 | 1.60 |
| 20 | $CH_2Cl_2$ | 23° c. | diglyme(i) | 6.0(e) | 1.4 | 1.51 |
| 21 | $CH_2Cl_2$ | 23° C. | diglyme(i) | 1.0(d) | 1.1 | 1.57 |

(a)Mole ratio of polyether to $NO_2BF_4$.
(b)As weight percent of total mononitrotoluenes as determined by gas chromatography. Less than 2% dinitrotoluenes were produced in any run with polyethers.
(c)Ortho-nitrotoluene to para-nitrotoluene ratio.
(d)Heterogeneous
(e)The minimum amount of polyether needed to make the solution homogeneous.
(f)cis-syn-cis-isomer (meso)
(g)cis-anti-cis-isomer (d,1)
(h)polyethylene oxide of 100 000 mol wt; used 1.80 g of polyether for 1.0 g of $NO_2BF_4$.
(i)bis-(2-methoxyethyl) ether, $CH_3O(C_2H_4O)_2CH_3$

EXAMPLES 22–24

These competition reactions were run by adding to a tenfold excess of a 1:1 mixture of toluene and benzene, the preformed homogeneous crown ether complexes of NO$_2$BF$_4$ in CH$_2$Cl$_2$ at 23° C. These experiments were performed and analyzed as described above.

Conductometric titrations of NO$_2$BF$_4$ with the crown ether in CH$_2$Cl$_2$ showed the stoichiometry in the soluble complexes to be 0.92 moles of 18-crown-6 per mole of NO$_2$+ and 3.0 moles of 12-crown-4 per mole of NO$_2$+. No well-defined stoichiometry for the 15-crown-5 complex of NO$_2$BF$_4$ in CH$_2$Cl$_2$ was detected but our results indicated a minimum of 1.7 moles of 15-crown-5 was needed to completely solubilize 1 mole of NO$_2$BF$_4$ in CH$_2$Cl$_2$ at 23° C. The 18-crown-6 and 15-crown-5/nitronium ion complexes in CH$_2$Cl$_2$ showed no visible signs of decomposition after 3 weeks under N$_2$ at room temperature However, the 12-crown-4 complex gave a tar after this period of time. All of the crown ethers showed some decomposition with the liberated HBF$_4$ after extended periods of time.

The nearly 1:1 stoichiometry of the 18-crown-6 NO$_2$+ complex suggests that the nitronium ion might be symmetrically complexed in the cavity of the crown. A new highly polarized band appeared at 880 cm$^{-1}$ in the Raman spectrum of the crown ether upon complexation with NO$_2$BF$_4$. This can been interpreted as arising from the symmetrical "breathing" mode of the ring in a highly symmetric complex in analogy with the K+ complex of 18-crown-6. Only a slight shift in the Raman symmetrical stretching frequency of NO$_2$+ from 1408 cm$^{-1}$ was noted upon complexation. The infrared spectrum of the 18-crown-6 complex showed bands at 3770 cm$^{-1}$, 2383 cm$^{-1}$, and 540 cm$^{-1}$ all characteristic of a linear nitronium ion. The strong asymmetric stretching frequency at 2383 cm$^{-1}$ of the complexed NO$_2$+ occurs at considerably higher frequency than uncomplexed NO$_2$+ (2340 cm$^{-1}$). In addition, a new band appeared in the spectrum at 1669 cm$^{-1}$ which might be due to a non-linear form of the nitronium ion. The spectra of the 15-crown-5 and the 12-crown-4 complexes showed no bands in the 2340–2383 cm$^{-1}$ region, but did show bands at 1640 cm$^{-1}$ and 1638 cm$^{-1}$, respectively. The Raman spectra of the 15-crown-5 and the 12-crown-4 complexes showed no bands at or near 1400 cm$^{-1}$. These observations indicate a bent or unsymetrically complexed form of the nitronium ion exists in these complexes.

To a 10 ml Erlenmeyer flask equipped for magnetic stirring was added 2 ml of 80 weight % H$_2$SO$_4$ (28.2 mmoles) in water (38.4 mm) and 0.530 g of 18-crown-6 ether (2 mmoles) obtained from Aldrich Chem. Co. The mixture was stirred for 30 minutes until all the crown dissolved. To the homogeneous yellow-brown solution at ambient temperature was slowly added 126 μl of 70 weight % HNO$_3$ (2 mmoles HNO$_3$) in water (3 mmoles). After 5 min., 320 μl of toluene were slowly added. The homogeneous red solution so formed was stirred for 30 min. at 30° C. Water (10 ml) was added and the resulting solution was extracted with 10 ml of CH$_2$Cl$_2$. The CH$_2$Cl$_2$ layer was dried over MgSO$_4$, condensed and analyzed by g.l.c. to consist of 257 mg (94% yield) of mononitro toluenes in the following proportions: 57.9% ortho-nitrotoluene, 2.8% meta-nitro toluene and 39.2% para-nitrotoluene. The ortho/para ratio was 1.48:1. The crown ether (490 mg, 93% of the initial amount) was recovered unchanged. No decomposition products were detected.

EXAMPLE 26

An experiment similar to Example 25 was run without any crown ether. By glc analysis, the mononitro toluenes consisted of 59.0% ortho, 3.3% meta and 37.5% para. The ortho/para ratio was 1.57:1.

EXAMPLE 27

Into a 10 ml flask was placed 321 mg (2.41 mmol) of NO$_2$BF$_4$ (Aldrich Chem. Co.) and 3.0 ml of CH$_2$Cl$_2$. To this slurry was added a solution of 662 mg (2.50 mmol) of 18-crown-6 in 1.5 l of CH$_2$Cl$_2$. After stirring at 25° C. a yellowish homogeneous solution was formed. To this solution was added 480 μl of 85% H$_2$SO$_4$ prepared by mixing 1.11 ml of 96% H$_2$SO$_4$ with 280 μl of H$_2$O. After stirring at 25° C., all the yellow color disappeared and two water-white layers were formed. The CH$_2$Cl$_2$ layer was removed with a syringe. The H$_2$SO$_4$ layer was stirred with 1 ml of fresh CH$_2$Cl$_2$, and the CH$_2$Cl$_2$ layer was removed and combined with the first CH$_2$Cl$_2$ layer.

To the combined CH$_2$Cl$_2$ layers was added 300 μl (2.81 mmol) of toluene. The homogeneous solution was stirred at 25° C. for 30 minutes, then quenched by the addition of excess water. The layers were separated; the

TABLE II

Competitive Nitration of Benzene and Toluene with Homogeneous NO$_2$BF$_4$—Crown Ether Complexes in CH$_2$Cl$_2$ at 23° C.

| Run | Crown Ether | Crown(1) NO$_2$+ in Complex | Benzene(2) NO$_2$+ | Toluene(2) NO$_2$+ | $k_T/k_B$(3) |
|---|---|---|---|---|---|
| 22 | 18-crown-6 | 1.0 | 10 | 10 | 59 |
| 23 | 15-crown-5 | 1.7 | 10 | 10 | 56 |
| 24 | 12-crown-4 | 3.0 | 10 | 10 | 45 |
| — | None | — | — | — | 1.7(4) |

(1)Mole ratio of crown ether to NO$_2$+ used to make the NO$_2$BF$_4$ completely soluble in CH$_2$Cl$_2$.
(2)Mole ratio of benzene and toluene to NO$_2$+ used. The solution of the complexed NO$_2$BF$_4$ in dichloromethane was added to a ten mole excess of a 1:1 mixture of benzene and toluene in CH$_2$Cl$_2$ with rapid stirring.
(3)Ratio of the relative rates of toluene nitration to benzene nitration.
(4)Taken from the work of G. A. Olah and N. A. Overchuk (Can. J. Chem., 43, 3279 (1965)) on nitrations with NO$_2$BF$_4$ in tetramethylene sulfone. This ratio could not be determined in CH$_2$Cl$_2$ without added crown ether due to the complete insolubility of NO$_2$BF$_4$ in CH$_2$Cl$_2$. However, this number probably represents an upper limit for $k_T/k_B$ in CH$_2$Cl$_2$.

EXAMPLE 25

(Homogeneous one phase nitration of toluene)

(4.1 moles of H$_2$SO$_4$ to 20.7 moles H$_2$O:1 mole of 18-crown-6:1 mole of HNO$_3$).

CH$_2$Cl$_2$ layer was dried. By glc analysis, the CH$_2$Cl$_2$ layer contained 17% yield of mononitro toluene consisting of 55.3% ortho, 2.0% meta and 42.5% para nitro toluenes. 328 mg of crown ether (49.5%) was recovered.

To the H₂SO₄ layer was added 2 ml of fresh CH₂Cl₂ and 300 μl of toluene (2.81 mmol) with rapid stirring. After 1 hour at 25° C., a bright yellow color developed in the CH₂Cl₂ layer. Stirring was continued for 3½ days at 25° C. After quenching with water, the CH₂Cl₂ layer was analyzed by glc to contain a 18.5% yield of mono nitrotoluenes consisting of 58.0% ortho, 1.9% meta and 40.0% para nitrotoluene; 350 mg of crown ether (50% of the initial amount) was recovered.

EXAMPLE 28

A homogeneous solution of NO₂⁺-crown complex was prepared by mixing 763.9 mg (2.05 mmol) of mesodicyclohexyl-18-crown-6 (Isomer A, mp 59°–61° C.) in 4.5 ml of dry CH₂Cl₂ with 271 mg (2.04 mmol) of NO₂BF₄ (Aldrich Chem. Co.) at ambient temperature. To this solution was added 410 μl (8.2 mmol) of 85% H₂SO₄. After stirring for one hour at ambient temperature (20°–21° C.) there remained gummy, white lower layer and a yellow CH₂Cl₂ upper layer. The layers were separated and to each was added 300 μl (2.81 mmol) of toluene.

The lower aqueous layer was stirred with toluene for 3½ days at ambient temperature, then quenched and analyzed by glc. No nitrated toluene products were detected. The amount of crown ether recovered was 17% of the initial amount added.

The yellow organic (CH₂Cl₂) layer was stirred for 2 hours at ambient temperature, then quenched by the addition of water and analyzed by glc. The yield of mononitro products was 30%; the amount of crown ether in the organic layer was 83% of that initially added. The mono-nitrotoluene mixture had the following composition: 59.0% ortho, 1.5% meta and 39.4% para-nitrotoluene; the ortho/para ratio was 1.50.

EXAMPLE 29

To a heterogeneous mixture of 387.7 mg (2.92 mmol) of NO₂BF₄ in 3.0 ml of CH₂Cl₂ was added 870 μl (17.4 mmoles) of 85% H₂SO₄ (17.4 mmole of H₂O). All of the NO₂BF₄ dissolved. The two layers formed were separated and 300 μl (2.81 mmol) of toluene were added to each layer. The organic layer was stirred for 2 hrs at ambient temperature, then quenched and analyzed by glc. No nitrated toluenes were detected.

After stirring the aqueous layer for 3½ day at ambient temperature, the reaction was quenched and analyzed by glc. The mono nitro toluene products (58% yield) were present as 59.6% ortho, 2.4% meta and 38.0% para nitrotoluene. The ortho/para ratio was 1.57.

TABLE III

| | NITRATIONS OF TOLUENE IN THE PRESENCE OF H₂SO₄—H₂O | | | |
|---|---|---|---|---|
| Run | System | Temperature | % meta (±.2) | Ortho para |
| 25 | H₂SO₄:H₂O:HNO₃: 18-crown-6(1) | 30° C. | 2.8 | 1.48 |
| 26 | H₂SO₄:H₂O:HNO₃(2) | RT(4) | 3.3 | 1.57 |
| 27 | H₂SO₄:H₂O— NO₂BF₄— 18-crown-6(2,3) | 25° C. | 2.0 | 1.30(5) |
| 28 | H₂SO₄—H₂O— NO₂BF₄—Dicyclohexyl-18-crown-6(2,3) | 25° C. RT(4) for 2 hrs. RT for 3½ days | 1.9 1.5 nd | 1.45(6) 1.50(5) —(6) |
| 29 | H₂SO₄—H₂O—NO₂BF₄ | RT (4) RT(4) for 3½ days | nd 2.4 | —(5) 1.57(6) |

(1) Homogeneous
(2) Heterogeneous
(3) Toluene and CH₂Cl₂ were added to each phase of the two phase system
(4) RT is room temperature which was 20–21° C.
(5) CH₂Cl₂ layer
(6) Aqueous layer

We claim:
1. A reagent for selective aromatic nitration which comprises a complex of a nitronium containing substance and at least a catalytic amount of a macrocyclic polyether in the presence of a solvent selected from the group consisting of CH₂Cl₂, CHCl₃, SO₂, CH₃NO₂, CH₃CN, (CH₂)₄SO₂, CS₂ and polyhaloalkanes having 1 to 8 carbons.

2. A reagent as described in claim 1 wherein the nitronium containing substance is selected from a group consisting of NO₂BF₄, NO₂PF₆, NO₂SbF₆, NO₂SF₆, NO₂CF₃SO₃, NO₂SnF₆ and NO₂AsF₆.

3. A reagent as described in claim 1 wherein the macrocyclic polyether is selected from the group consisting of dicyclohexano-18-crown-6 and crown ethers having from 4 to 10 -O-M units wherein M for a particular macrocyclic polyether is

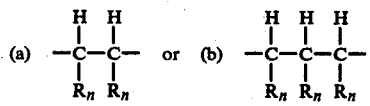

wherein each $R_n$ is independently selected from the group consisting of hydrogen or an alkyl group consisting of 1 to 4 carbons or wherein at least one M is (b) and the remaining are (a).

4. A reagent as described in claim 3 wherein the macrocyclic polyether is at least one of the members of the group selected from 12-crown-4, 15-crown-5, 18-crown-6 and meso- and d,l-dicyclohexano-18-crown-6.

5. A reagent as described in claim 3 wherein the macrocyclic ether is 18-crown-6.

6. A reagent is described in claim 5 wherein the crown ether and the nitronium substance are in a molar ratio of about 1 to 1.

7. A reagent as described in claim 3 wherein the macrocyclic ether is 15-crown-5.

8. A reagent as described in claim 7 wherein the crown ether and the nitronium containing substance are in a molar ratio of about 1.7 to 1.

9. A reagent as described in claim 3 wherein the macrocyclic ether is 12-crown-4.

10. A reagent as described in claim 9 wherein the crown ether and the nitronium containing substance are in a molar ratio of about 3.0 to 1.

* * * * *